United States Patent [19]

Sforza

[11] 4,053,362
[45] Oct. 11, 1977

[54] BACTERIAL ISOLATION METHOD AND DEVICE

[76] Inventor: Anthony Sforza, 804 E. 16th St. No. 6A, San Bernardino, Calif. 92404

[21] Appl. No.: 672,852

[22] Filed: Apr. 2, 1976

[51] Int. Cl.² ............................ C12K 1/04; C12K 1/10
[52] U.S. Cl. ............................... 195/103.5 R; 195/139
[58] Field of Search .................. 195/103.5 R, 127, 139

[56] References Cited

U.S. PATENT DOCUMENTS 3,715,280  2/1973  Farmer ........................ 195/103.5 R Primary Examiner—Raymond N. Jones
Assistant Examiner—Robert J. Warden
Attorney, Agent, or Firm—Henry M. Bissell

[57] ABSTRACT

The present improved bacterial isolation device comprises a bacterial test container with closed bottom, raised sides and open top. A honeycomb type isolation grid providing a plurality of isolated cells is embedded in a layer of non-nutritive medium covering the bottom of the container, so that swarming types of bacteria cannot pass from one isolated cell to another and thus grow over bacteria to other isolated cells and mask them from detection.

The improved method and device involve the disposition of a non-nutritive layer in the bottom of the container, covered with a separate layer of selected nutritive medium substantially unmixed therewith and introducing bacteria to the nutritive layer and embedding the isolation grid in the non-nutritive layer, covering the container and incubating the bacteria therein until they can be detected in the isolated grid cells. The method is simple, rapid, can be carried out with readily available, low-cost materials and eliminates both the requirements for a repeat test and for the use of bactericidal or bacteriostatic agents and the like in the nutritive medium to selectively suppress swarming bacteria.

16 Claims, 3 Drawing Figures

BACTERIAL ISOLATION METHOD AND DEVICE

BACKGROUND OF THE INVENTION

1. Field of the Invention

The present invention generally relates to test methods and devices and more particularly to improved bacterial isolation test methods and devices.

2. Description of the Prior Art

Certain conventional methods for isolating bacteria from body excretions, fluids, tissues, etc. in the detection of diseases usually include the addition to the nutritive culture medium of carefully selected amounts and types of bactericidal, bacteriostatic or similar agents which eliminate or inhibit the development of unwanted or interfering bacteria from the test field, particularly when swarming bacteria, such as various proteus species, may be present, as in cervical or rectal cultures. Swarming bacteria have the ability to migrate and overgrow and thus obscure non-migrating types of bacteria. When isolation grids are used to divide the culture into a series of isolated areas, the swarming bacteria in one or more such areas still can readily migrate through the nutritive medium and under the grid, even if only a microscopic gap exists between the grid and the test container in which the grid is disposed. The bacteria then overgrow other bacteria in other isolated grid areas, thus rendering the test useless. The correct selection and use of bactericical or bacteriostatic agents, etc. requires skill and may result in the elimination or inhibition of other bacteria which are possibly pathogenic and therefore important to the diagnosis and which otherwise might have been detected in the test. Accordingly, it has been a frequent practice of running a second bacterial isolation test under usually modified conditions, e.g. by changing or eliminating the bactericidal and bacteriostatic agents, not only to confirm the first test's results, but to increase the likelihood of detecting other pathogenic bacteria masked by putting in such agents. Such double test procedures are expensive and time consuming, utilizing expensive chemicals, antibiotics and the like, and are subject to a certain degree of error. Accordingly, there has been a need for a simple, inexpensive, rapid and more effective bacterial isolation method and device for detecting bacteria in a culture in which swarming interfering bacteria may be present.

Attempts have been made as shown in the prior art to provide simultaneous multiple tests in a single container having a common culture supporting medium. The Farmer U.S. Pat. No. 3,715,280 discloses such an arrangement which uses a cellular divider inserted into a container having a homogeneous culture supporting medium therein. The respective walls of the container and the divider are said to be configured to fit closely together. However this fails to guarantee the desired isolation between cells, particularly where swarming bacteria are to be cultured, since minute gaps providing inter-cell bacteria growth channels are inevitable. Moreover, such an arrangement requires especially configured dividers and container to try to achieve isolation and cannot make use of the commonly available, low-cost Petri dishes which generally have somewhat irregular and uneven interior wall and bottom surfaces.

Special multi-cell structures for achieving the desired isolation between individual cells are disclosed in Brown et al. U.S. Pat. No. 3,107,204 and Fink U.S. Pat. No. 3,632,478, for example. These structures incorporate the dividers integrally with the container so that the container comprises a plurality of separate sections. While these may be effective for the purpose intended, they appear to be considerably more expensive to fabricate than the patented structure described above and would not work when swarming bacteria are involved, since in streaking these cells one cannot insure there are no swarming bacteria in the cells.

Still another proposed solution to the problem of providing isolation between multiple test cells is disclosed in Saxholm U.S. Pat. No. 3,791,930. However, as with the others, effective isolation depends on establishing sealing contact between the cell walls and the bottom of the container. Any minute gap voids the desired isolation and renders the device ineffective, at least for use with swarming bacteria cultures.

SUMMARY OF THE INVENTION

The foregoing needs have been satisfied by the method and device of the present invention. The method and device are substantially as set forth in the Abstract above. In this regard in accordance with a first preferred embodiment of the present method, a layer of non-nutritive material which is embeddable by an isolation grid is poured or otherwise disposed in the bottom of a test container, such as a Petri dish, to fully cover the same to a desired predetermined depth. The bacterially nutritive medium for the culture is then added as a separate layer on top of the non-nutritive layer, and a bacterial smear, inoculation or the like is used to transfer the bacteria to be tested to the nutritive medium. Alternatively, the bacteria may already be present in the nutritive medium when the latter is added to the test container. An isolation grid is embedded in the non-nutritive layer but with its upper edge above the top of the nutritive layer. The resulting assembly is then covered and the bacteria therein are incubated until their colonies can be detected in the various isolated areas of the grid.

Swarming bacteria, when present, cannot cross from one isolated grid area to another, because they cannot migrate through either the grid or the non-nutritive layer. Accordingly, they cannot overgrow bacteria in a given isolated grid area when the swarming bacteria are not initially present in that isolated grid area. Thus, the method eliminates the need for bactericidal and bacteriostatic agents and repeat cultures without these agents present, all at a considerable saving of time, labor and expense.

The improved device of the present invention comprises the test container with the non-nutritive layer covering the bottom of the container and the isolation grid embedded in the non-nutritive layer.

In accordance with a second embodiment of the present method, the above-described components are first assembled together and then the bacteria is introduced in the nutritive medium to each isolated grid area, as by pipetting or the like. Similar advantages are obtained as in the first preferred embodiment, except that time is needed to carry out the pipetting. However, various dilutions of the bacterial test material may in any event be desired in order to simultaneously test the same for a quantitative measurement of the bacterial concentration. This can be accomplished easily utilizing this second preferred embodiment of the present method.

BRIEF DESCRIPTION OF THE DRAWING

A better understanding of the present invention may be had from a consideration of the following detailed description, taken in conjunction with the accompanying drawing, in which.

DESCRIPTION OF THE PREFERRED EMBODIMENTS

Figure 1:
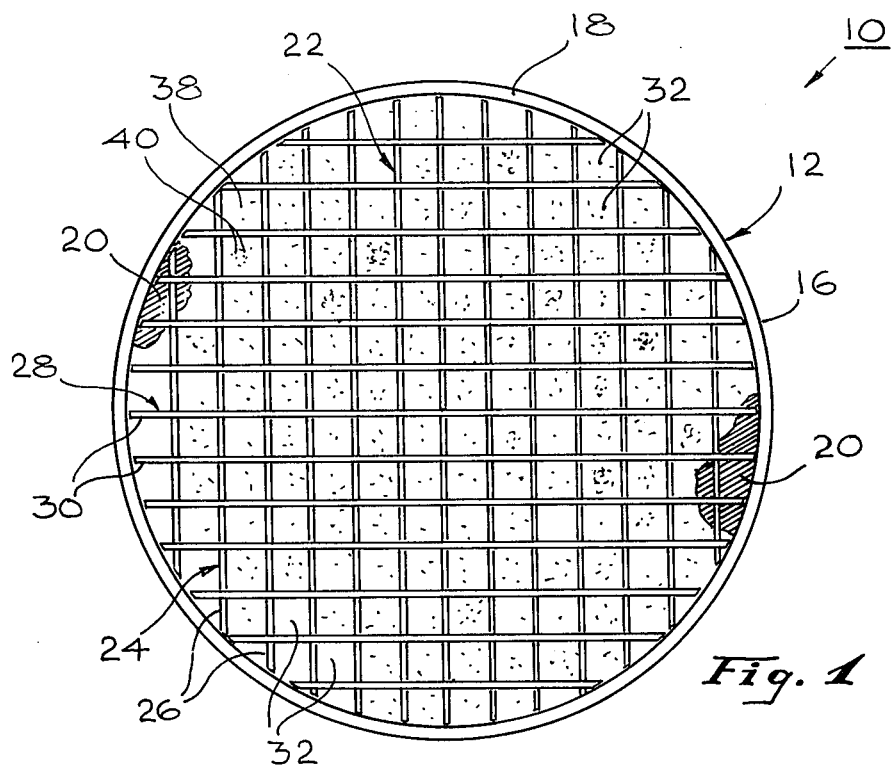
FIG. 1 is a schematic top plan view, somewhat enlarged, of a first preferred embodiment of the improved bacterial isolation device of the present invention, with the top cover thereof removed.
Figure 2:
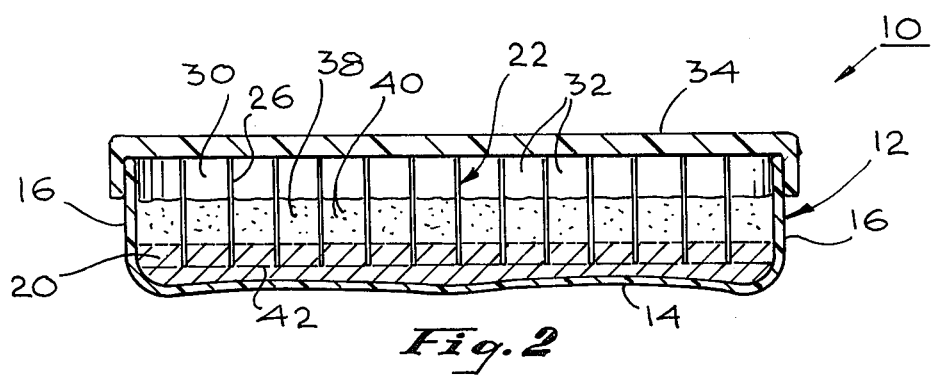
FIG. 2 is a schematic side elevation in partial section, somewhat enlarged, of the device of FIG. 1 with the top cover in place and with bacteria-laden nutritive medium in the device for incubation, growth, isolation and detection of the bacteria.

Now referring more particularly to FIGS. 1 and 2 of the drawings, a first preferred embodiment of the improved bacterial isolation device of the present invention is schematically depicted therein in top plan view. Thus, device 10 is shown which includes a transparent test container 12 of glass, plastic or the like, preferably circular in outline, and having a closed bottom 14, raised peripheral sidewalls 16 and an open top 18. It will be noted that bottom 14 is somewhat irregular or multi-planar with rounded corners, as is usually the case with inexpensive glass containers, some plastic containers, etc., such as Petri dishes, which are used in great quantities in laboratories and which may be of the single use or multiple use type.

Device 10 further includes a layer 20 of bacterially non-nutritive embeddable medium, such as paraffin wax, or a mixture of paraffin wax and petroleum jelly or the like, which preferably is solid at ambient temperature but is easily sterilizable and pourable as a liquid into container 12 to completely cover and conform to the shape of the bottom 14 thereof, as shown in FIG. 2. Layer 20 should be sufficiently soft when set to permit isolation grid 22 which forms part of the present device to be easily embedded in and supported by the same (FIG. 2). Grid 22 comprises a first set 24 of spaced parallel walls 26 and a second set 28 of spaced parallel walls 30 intersecting walls 26 preferably at a right angle and connected thereto so as to define a plurality of open-topped and open-bottomed isolated grid cells or areas 32 of about equal dimensions. The grid 22 may comprise a metal honeycomb material, such as is commonly used in aircraft laminated members.

As shown, device 10 comprises the container 12, layer 20 disposed therein and grid 22 embedded in layer 20. Device 10 may also include a removable top cover plate 34 (FIG. 2).

It will be noted that cover plate 34 can be dimensioned so that it can be used to push grid 22 down into layer 20 as shown in FIG. 2. It will be further noted that FIG. 1 depicts device 10 with cover plate 34 removed and with device 10 ready for use in one embodiment of the improved bacterial isolation method of the present invention. FIG. 2 depicts device 10 during the use in the bacterial isolation method of the present invention with a bacterially nutritive layer 38 of, for example, an enriched agar-agar medium, blood-agar, or an enriched broth or other bacterial growth medium containing bacteria 40 to be identified disposed on the top of layer 20 and substantially unmixed therewith. Device 10 in FIG. 2 is ready for incubation of bacteria 40, cover plate 34 being in place on container 12.

In carrying out the present method, the bacterially non-nutritive medium layer 20 is first disposed in the bottom 14 of container 12 so as to cover bottom 14, after which the following steps are carried out in one suitable sequence or combination: covering the non-nutritive layer 20 with a nutritive layer 38, introducing bacteria into container 12 and layer 38 by a routine method of streaking for isolation or a pour technique, for example, and embedding the grid 22 into layer 20 (possibly through layer 38), the arrangement being such that the top of grid 22 is above the top layer 38. Thus, grid 22 can be embedded in layer 20 before layer 38 and bacteria 40 are added, as by pipetting into areas 32, to container 12. Alternatively, layer 38 can be added to container 12 before or with bacteria 40, after which grid 22 can be embedded into layer 20. In any event, in accordance with the present method, it is usual then to cover the container 12, as by cover plate 34, and incubate the bacteria 40 in container 12 until the bacterial colonies can be detected in the various isolated areas 32. It will be noted that all walls 26 and 30 of grid 22 have their bottoms embedded in layer 20 so that swarming bacteria which may be present in one or more cells or areas 32 cannot pass under walls 26 and 30 and migrate to other areas 32 and then obscure the test results by growing over other bacteria in those other areas 32. The non-nutritive nature of layer 20 completely prevents such passage of swarming bacteria, even though one or more gaps 42 exist (FIG. 2) between the bottom of grid 22 and the bottom of container 12. Gaps 42 are effectively filled with the non-nutritive medium of layer 20. Accordingly, the bacterial incubation can proceed without fear of overgrowth of swarming bacteria and in the absence of expensive selective bactericides, bacteriostats, etc. Moreover, only a single test need be run for a proper diagnosis, since without such bactericides and bacteriostats and without swarming bacterial overgrowth there is no danger of failing to detect one or more other possibly pathogenic bacteria in areas 32, in addition to the bacteria mainly sought in the isolation test. Accordingly, the present method and device 10 result in a substantial saving of time and expense and yet yield accurate results.

Figure 3:
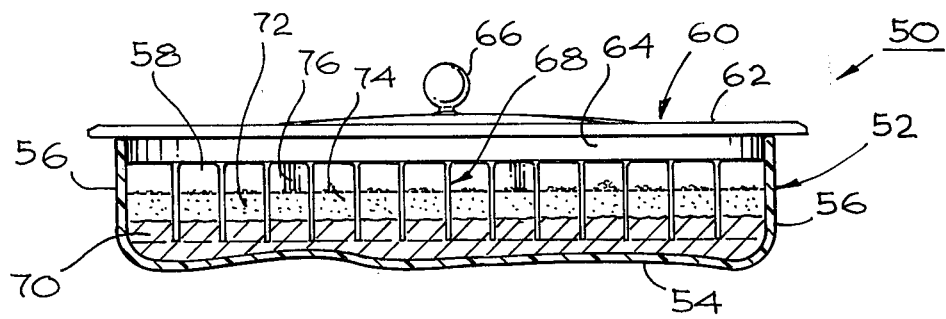
FIG. 3 is a schematic side elevation, in partial section, somewhat enlarged, of a second preferred embodiment of the improved bacterial isolation device of the present invention, with its top cover in place, and with bacteria-laden nutritive medium in the device for incubation, growth, isolation and detection of the bacteria.

A second preferred embodiment of the improved bacterial isolation device of the present invention is schematically illustrated in side section elevation in FIG. 3. Thus, device 50 is depicted which includes a generally rectangular, shallow container 52 of glass, transparent plastic or the like with a bottom 54, which may be irregular (as shown) or uniplanar, raised sides 56 and an open top 58, covered by a removable cover plate 60 of similar material to container 52. Cover plate 60 comprises a top 62 overlying and extending beyond sides 56 and a recessed portion 64 releasably fitting against the upper inner margins of sides 56, as shown in FIG. 3, in a manner which permits air to enter the container 52. A handle 66 extends up from top 62 and a grid 68 of glass, plastic, metal or other inert substance substantially identical in construction (although rectangular in outline to conform to container 53) to grid 22 is secured to and depends from the underside of recessed portion 64, so that when cover plate 60 is in place, as in FIG. 3, grid 68 is embedded in a layer 70 of bacterially non-nutritive medium (similar to layer 20) covering the entire bottom 54 of container 52. A layer 72 of bacterial nutritive medium (similar to layer 38) is disposed directly on the top of layer 70 and contains bacteria 74 to be detected through the use of device 50.

When device 50 is used in accordance with the present method, layer 70 is first added as a liquid to open container 50, after which it may be allowed to set and then layer 72 is added, with or without bacteria 74. If bacteria 74 are added separately to container 50, the surface or subsurface of layer 72 is streaked or otherwise inoculated with bacteria 74. Thereupon, cover plate 60 is fixed in place so that the assembly is sealed from contamination and, as shown in FIG. 3, the bacteria 74 are then incubated in accordance with conventional procedure in container 52 until they can be detected in the conventional manner in the various isolated cells 76 of grid 68. The cover 60 and grid 68 are releasably attached together to permit separation after the culture is grown. Generally after the culture is grown, the isolated colonies are picked off with a wire loop and sub-cultured in various test media or examined under a microscope to identify the bacteria.

Device 50 is simple, inexpensive, easy to use and highly effective. It prevents, in the same manner as device 10, swarming bacteria from migrating from one cell 76 to other cells 76 and thus obscuring other types of bacteria in those other cells 76, and it eliminates the need for multiple tests and for bactericidal and bacteriostatic agents, and thus has the same advantages as device 10. Other features and advantages of the device and method of the present invention are as set forth in the foregoing.

Various modifications, changes, alterations and additions can be made in the present device, its components and parameters and in the present method, its steps and parameters. All such modifications, changes, alterations and additions as are within the scope of the appended claims form part of the present invention.

What is claimed is:

1. An improved bacterial isolation device comprising, in combination:
   a bacterial test container having a closed bottom, raised sidewalls and an open top;
   a layer of predetermined thickness of a bacterially non-nutritive medium covering said bottom, said medium being of an embeddable consistency; and
   an isolation grid comprising a first set of spaced walls intersected by and connected to a second set of spaced walls to form a plurality of isolated test cells, said grid having all its walls embedded in said medium, whereby during use of said device swarming bacteria are prevented from passing under said grid from one said isolated area to any other of said isolated areas to overlie and mask other bacteria.

2. The improved device of claim 1 wherein said non-nutritive medium is bacterially non-nutritive and comprises a wax which is liquid at elevated temperature but solid at ambient temperature.

3. The improved device of claim 2 wherein said non-nutritive medium includes petroleum jelly.

4. The improved device of claim 3 wherein said non-nutritive medium comprises a mixture of paraffin and petroleum jelly.

5. The improved device of claim 1 wherein said grid comprises a honeycomb section and wherein said grid substantially fills an area defined by said container sidewalls.

6. The improved device of claim 1 wherein said device includes a detachable cover plate.

7. The improved device of claim 6 wherein said grid is releasably connected to the underside of said cover plate and is embedded in said non-nutritive medium to only a predetermined depth.

8. The improved device of claim 1 wherein said container comprises a Petri dish.

9. The improved device of claim 8 wherein the bottom of said Petri dish is irregular and non-planar.

10. The improved method of isolating bacteria for test purposes, said method comprising:
    disposing a layer of embeddable bacterially non-nutritive medium in a bacterial test container so as to fully cover the bottom of said container to a predetermined depth;
    covering said layer of non-nutritive medium with a separate layer of desired bacterial nutritive medium;
    adding bacteria to the top of the nutritive medium;
    embedding the bottom of an isolation grid in said non-nutritive medium, the upper edge of said grid being above the level of said nutritive medium to define a plurality of isolated test cells; and
    covering said container and incubating bacteria therein until the bacteria can be detected in said isolated test cells.

11. The improved method of claim 10 wherein said bacteria are already in said nutritive medium when introduced into said container.

12. The improved method of claim 11 wherein said isolation grid is embedded in said non-nutritive medium before said bacterial introduction.

13. The improved method of claim 10 wherein said non-nutritive medium is bacterially non-nutritive and comprises a wax which is readily sterilizable as a liquid at elevated temperature but is solid at ambient temperature.

14. The improved method of claim 13 wherein said medium includes petroleum jelly.

15. The improved method of claim 14 wherein said non-nutritive medium comprises a mixture of paraffin and petroleum jelly.

16. The improved method of claim 10 wherein said non-nutritive and nutritive layers are kept substantially separate and unmixed so that channels of nutritive medium are not provided in said non-nutritive layer through which swarming bacteria can migrate between isolated grid areas.

* * * * *